United States Patent [19]

Baumberg

[11] Patent Number: 4,667,681

[45] Date of Patent: May 26, 1987

[54] PULSE RATE MONITOR

[76] Inventor: Iosif Baumberg, 54 Bay 29 St. #B5, Brooklyn, N.Y. 11214

[21] Appl. No.: 757,296

[22] Filed: Jul. 22, 1985

[51] Int. Cl.$^4$ ................................................ A61B 5/02
[52] U.S. Cl. ..................................................... 128/689
[58] Field of Search .............. 128/689, 690, 702, 703, 128/706, 707

[56] References Cited

U.S. PATENT DOCUMENTS

| | | | |
|---|---|---|---|
| 3,658,055 | 4/1972 | Abe et al. | 128/703 |
| 3,820,025 | 6/1974 | Lahr et al. | 128/706 |
| 3,952,731 | 4/1976 | Worstewcroft | 128/702 |
| 4,022,192 | 5/1977 | Laukign | 128/706 |
| 4,202,350 | 5/1980 | Walton | 128/690 |
| 4,367,752 | 1/1983 | Jimenez et al. | 128/706 |
| 4,489,731 | 12/1984 | Baumberg | 128/690 |
| 4,566,461 | 1/1986 | Lubell et al. | 128/707 |

Primary Examiner—William E. Kamm
Attorney, Agent, or Firm—Ilya Zborovsky

[57] ABSTRACT

A pulse rate monitor has an electronic histogram unit, an averaging unit including a clock generator and two sets of counters with a set of dividers therebetween. Each set of counters and dividers is provided with display devices. Switching and controlling elements are provided to interconnect respective sets and units of the monitor for various modes of operation.

8 Claims, 2 Drawing Figures

PULSE RATE MONITOR

BACKGROUND OF THE INVENTION

The present invention relates in general to a pulse rate monitor and, in particular, to a monitoring device which provides for the concurrent analysis and display of pulse rate and variations thereof.

Monitoring devices of this kind are known in the art. One of such devices is disclosed in my U.S. Pat. No. 4,489,731 and designed such that it can be worn by a user. This device employs a histogram unit displaying the distribution of time intervals between successive heart beats of a user, and also measures and displays an average frequency of the heart beats. The prior art monitor, however, determines the histogram of time interval distributions without regard to outside factors affecting the user, particularly without regard to the magnitude and change in the time of physical load applied to the user. The applied load or actions performed by the user can be measured for example, by the number of paces of a walking person, by a number of revolutions of bicycle pedals or wheels, by the number of particular movements of an exerciser and the like.

SUMMARY OF THE INVENTION

It is therefore a general object of the present invention to provide a pulse rate monitor which avoids the disadvantages of the prior art.

More particularly, it is an object of the present invention to provide a pulse rate monitor by means of which it is possible to determine the frequency of heart beats of a user as a function of frequency of physical actions performed by the user irrespective of changes in frequency of such actions (for example, regardless of the frequency of paces of a walking person); as a function of a total number of individual actions performed by a user (expressed for example, as a total number of paces, a total number of bicycle revolutions etc., counted from the beginning of the measurement; and as a function of the duration of physical actions or loads expressed for example, as a total elapsed time of walking, exercising, etc.

In keeping with these objects and with others which will become apparent hereinafter, one feature of the present invention resides, briefly stated, in a combination which comprises a first detector for a first sequence of pulses; an electronic histogram unit having an input and a plurality of output channels corresponding to predetermined pulse spacings; a set of first counters and a set of second counters each having a data input and a plurality of data outputs and each being provided with with display means, the first and second counters being assigned to respective output channels of the histogram unit; a set of dividers connected between the outputs of the first and second counters to produce quotients of counts of the latter, each of the dividers being provided with display means; a clock pulse generator; a second detector for a second sequence of pulses; switching means having a first switching position in which the first detector is connected to the input of the histogram unit, the inputs of the first counters are connected, respectively, to the output channels and the second counters being connected in series with the averaging unit, and a second switching position in which the first detector is connected to each input of said first counters, said second detector is connected to the input of said histogram unit, and the inputs of said second counters are connected to an output of said clock pulse generator; and control means for controlling the connection between said first detector to said first counters and the connection between said clock pulse generator and said second counters to activate, in the second position of said switching means, those first and second counters which pertain to an active output channel of said histogram unit.

The novel features of the present invention are set forth in particular in the appended claims. The invention itself, however, will be best understood from the following description of a prefferred embodiment when read in connection with the accompanying drawings.

DESCRIPTION OF A PREFERRED EMBODIMENT

Figure 1:
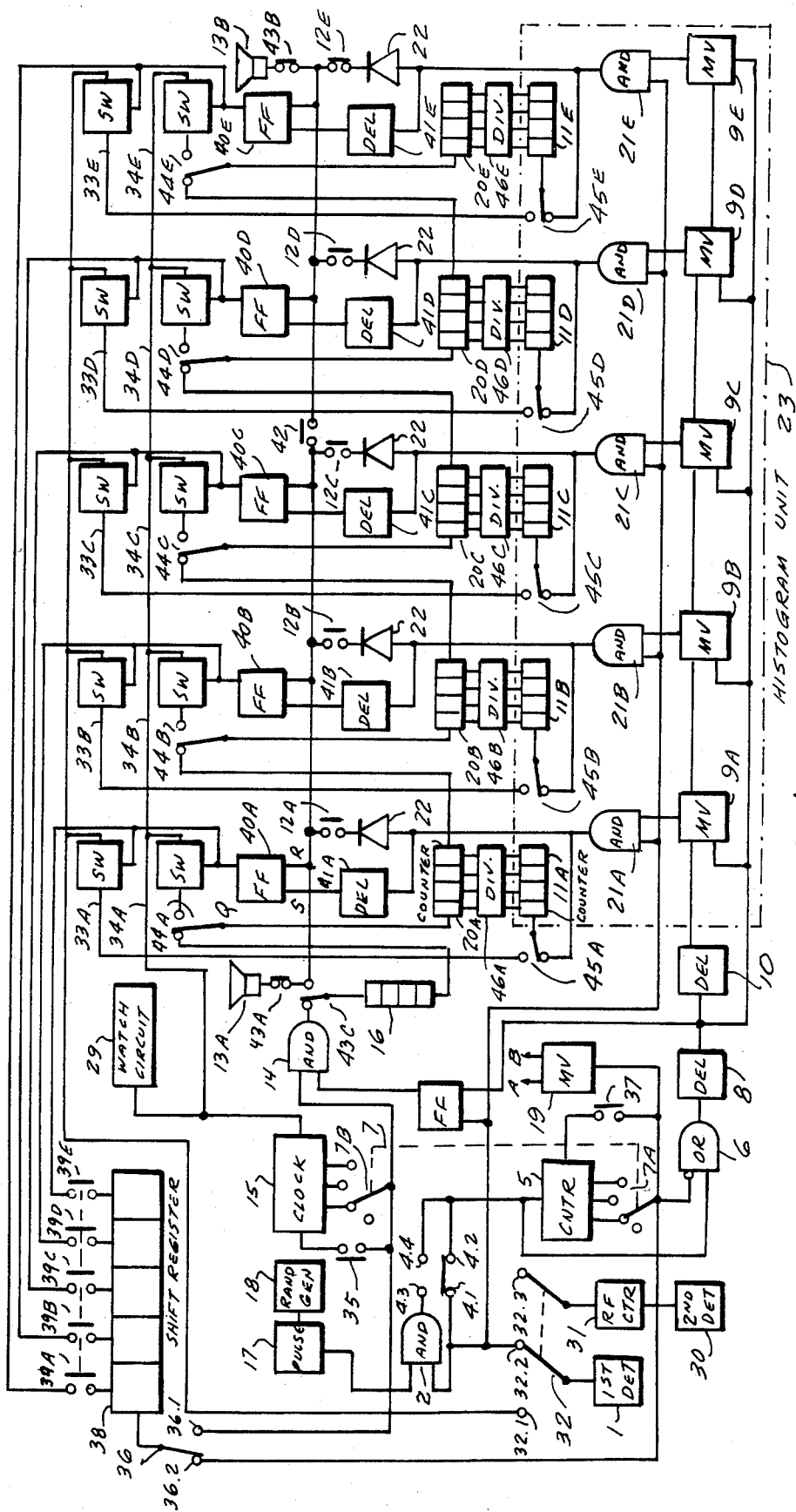
FIG. 1 is a circuit diagram of a pulse rate monitor according to the present invention.

Referring now to FIG. 1, circuit elements 1 through 29 correspond in structure and operation to those described in the U.S. Pat. No. 4,489,731, whose entire disclosure is incorporated here by reference. More particularly, in the lower position of switch 4, and in the illustrated position of switch 32, pulses from heart beat detector are fed directly via "OR" gate 6 and delays 8 and 10 into histogram unit 23 which displays distribution of different heart beat spacings in corresponding display devices pertaining to channels A–E. At the same time the pulse intervals are set by a user in dependence upon numbers of impulses desired to be counted by switch 76, and the average value determined by counters 20A–20E in cooperation with clock pulse generator 15 are displayed in windows corresponding to the location of display windows pertaining to counters 11A–11E of the histogram unit. In the upper position of switch 4, the heart beat spacings are measured at random (statistical mode of operation).

In this manner, the user can distinguish between indications showing regular heart activity or irregular one (arrhythmia) and can also determine whether the arrhythmia is symmetrical or assymetrical.

According to this invention, the prior art heart monitor is further improved to take into account the effect of discrete external action performed by the user during the heart beat measurement. For this purpose there is provided a second detector 30 which detects such actions. e.g. the numbers of pedal strokes when the user is riding a bicycle, or the number of paces when walking or jogging and the like, and generates a sequence of corresponding electrical pulses. The output of the detector 30 is connected to a recounting device 31 operating with a recounting factor k=1,2, . . . n, to pass through each k-th pulse from the detector 30. The recalculated sequence of pulses from the device 31 is applied to an arm of a double pole two position switch 32 whose other arm is connected to the heart beat detector 1. When the position of the arms of the switch 32 is changed, detector 1 is switched over from terminal 32.2 to terminal 32.1, and the output of the device 31 is switched over from the floating terminal 32.3 to the terminal 32.2.

Terminal 32.1 is connected via a first set of normally open, electrically controlled switching devices 33A–33E (e.g. switching transistors) and via two-position switches 45A–45E to the inputs of respective counters 11A–11E in the histogram unit 23.

A second set of normally open, electrically controlled switching devices 34A–34E (transistors, e.g) is connected to the output of clock pulse generator 15 to connect the same, via switches 44A–44E in series with the inputs of respective counters 20A–20E of the averaging unit. The zeroing input of the clock pulse generator 15 is connected via pushbutton switch 35 to a contacts 36.1 of a two-position switch 36 whose switching arm is connected to the input of a shift register 38 having as many stages as many channels A–E has the histogram unit 23. The contact 36.1 of switch 36 is connected to switching arm of selector switch 7B and to an input of AND gate 14. The other contact 36.2 of switch 36 is connected to switching arm of selector switch 7A, to an input of OR gate 6, to multivibrator 19, and via pushbutton switch 37 to zeroing input of counter 5.

The outputs of the stages of the shift register 39 are connected, via gang switches 39A–39E, with controlling inputs of the first and second sets of switching devices 33A–33E, whose switching condition is thus controlled by the outputs of the individual stages of the shift register 38. In addition, the controlling inputs of switching devices 33A–33E and 34A–34E are also connected with Q outputs of respective RS flip-flops 40A–40E.

The setting inputs S of the flip-slops 40A–40E are connected via delay devices 41A–41E with outputs of respective AND gates 21A–21E of the histogram unit 23. Each two-position switch 44A–44E connects in its first position counters 16 and 20A–20E in series with the output of AND gate 14, and in its second position connects the individual switching devices 34A–34E with the data input of assigned counters 20A–20E. Each two-position switch 45A–45E connects in its first position the inputs of the respective counters 11A–11E with the outputs of AND gates 21A–21E, whereby the monitor operates in the same manner as disclosed in the U.S. Pat. No. 4,489,731. In the second position of the switches 45A–45E the inputs of the pulse counters 11A–11E are connected via electronically controlled switching devices 33A–33E with the terminal contact 32.1 switchable to detector 1.

Figure 2:
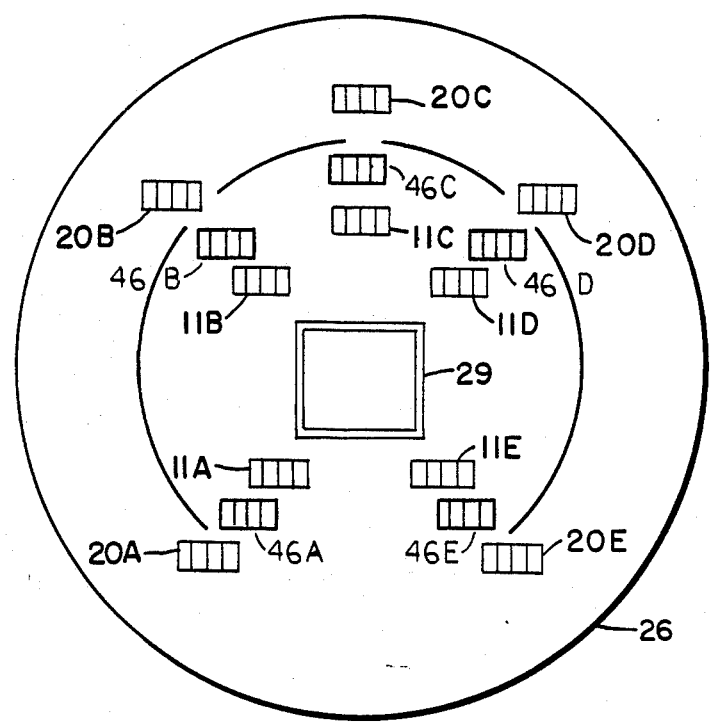
FIG. 2 is a layout of a display panel of the monitor of FIG. 1 of the invention.

The outputs of the counters 11A–11E are electronically compared with the outputs of the counters 20A–20E in dividers 46A–46E. Each divider 46A–46E is also provided with a display device and decoding circuits, similarly as are the counters 11A–11E and 20A–20E. The outputs from counters 11 serve as dividents whereas the outputs from counters 20 serve as divisors, and the resulting quotients are displayed in the display windows of respective dividers 46A–46E as indicated in FIG. 2.

As a result of various combinations of switching positions of the manually operable switches of the monitor, the latter can be adjusted to operate in four different modes of operation.

For setting the first mode of operation shown in FIG. 1, switches 35,37,39A–39E,42 are open, switches 43A and 43B are closed, switch 43C is in its shown position in which it connects AND gate 14 with the counter 16 switch 32 is in the illustrated first position in which the detector 1 is connected to the terminal 32.2 while terminals 32.1 and 32.3 are floating. Switches 44A–44E are in the illustrated first position in which all counters 20A–20E and 16 are connected with one another in series, switches 45A–45E are in the illustrated first position in which each AND gate 21 of the histogram unit 23 is connected to the input of the assigned counter 11A–11E.

For setting the second mode of operation the switches 35,37,39A–39E,43A,43B are open, switches 12A–12E, switch 42 are closed, the switch 32 is in the second position in which the detector 1 is connected via the terminal 32.1 with the inputs of all electronically controlled switching devices 33A–33E of the first set, the output of the recounting device 31 is connected via the terminal 32.2 with an input of the AND gate 2 and through closed contacts 4.1 and 4.2 to another input of OR gate 6 whose output is fed via delays 8 and 10 to the input of histogram unit 23. The switches 45A–45E are in the second position in which the first set of switching devices 33A–33E is connected with the inputs of respective pulse counters 11A–11E, the switches 44A–44E are in the second position in which the second set of switching devices 34A–34E is connected with the respective inputs of the pulse counters 20A–20E, the arms of the switches 7A–7B are set to a floating position disconnected from the clock pulse generator 15 and counter 5.

For setting the third mode of operation the switches 35,37,39A–39E, switch 42 are closed, the switches 12A–12E,43A, 43E are open, the switches 32,44A–44E, 45A–45E are in the second position, the switch 36 is in the second position in which the input of the shift register 38 is connected via the terminal 36.2 with the arm of the switch 7a.

The fourth mode of operation differs from the third mode in that the switch 36 is in the first position in which the input of the shift register 38 is connected via the terminal 36.1 with the arm of the switch 7B.

The switching positions which are not specifically described are of no consequences for performing the functions of the respective modes.

In the first mode of operation the monitor operates in correspondence with the operation described in the U.S. Pat. No. 4,489,731. The device computes an average frequency of pulse beats and distribution of time spacings between the successive pulse beats in the channels A–E of the histogram unit 23. The data delivered by pulse counters 11A–11E and 20A–20E are displayed in corresponding windows shown in FIG. 2.

In the second mode of operation the pulses from the detector 1 are supplied through the terminal 32.1 to all switching devices 33A–33E. Each k-th impulse from the detector 30 of physical actions passed through the recounting device 31 is supplied via terminal 32.2 immediately to an input of all AND gates 21A–21E and via OR gate 6 and delays 8 and 10 through consecutive channels A–E of the histogram unit 23. The channels A–E have such time width that impulses of heartbeat with different time intervals between the impulses pass through different channels. The width of channels A–E of the unit 23 is determined as $$T_i = \sum_{j=m+1}^{m+k} \tau_j,$$

wherein
k is a coefficient of recounting of the impulses performed by the recounting device 31($k=1,2,\ldots,n$),
$m=k, 2k, 3k, \ldots$, and $\tau_j$ is a magnitude of j-th time interval between two closest successive impulses from the detector 30 or the time duration of j-th physical action or load.

The appearance of logic 1 at the output of any AND gate 21A–21E leads to the logic 1 simultaneously at R inputs of all flip-flops 40A–40E while, due to the action of delays 41A–41E the setting inputs are at logic 0. Consequently, the Q outputs of all flip-flops 40A–40E switch to the logic 0. This signal 0 is applied to the controlling inputs of all normally open switching devices 33A–33E and 34A–34E and the latter remain in their open condition. After termination of the signal 1 (heart beat) at the zeroing inputs R of all flip-flops 40A–40E as a result of the delaying action of the delay element 41A–41E, the flip-flop 40A–40E pertaining to a channel which supplies the signal 1 from the output of the corresponding AND gate, receives that signal 1 at its setting input S while the resetting input R is at 0. Consequently, the output Q of this flip-flop 40A–40E is set to logic 1 and the controlling inputs of the corresponding switching devices 33A–33E and 34A–34E are activated and the two devices are switched over to a closed position. During the conducting condition of the switching devices 33A–33E and 34A–34E the counter 11A–11E in the corresponding channel counts the heart beats of the user received from detector 1 through the switching device 33A–33E, and the counter 20 of this channel starts counting the impulses at the intervals supplied through the second switching device 34A–34E from the clock generator 15.

Example: Let us assume that signal 1 is supplied from the output of the AND gate 21C and switches 12A–12E from the output of the element 21C is simultaneously supplied to all resetting inputs R of all flip-flops 40A–40E, and as a result the Q outputs of the flip-flops 40A–40E are switched to the logic 0, and all normally open switching devices 33A–33E and 34A–34E remain in their open position. After termination of the logic 1 condition at the output of the element 21C, because of the delay element 41C, the logic 1 state is received at the setting input S of the flip-flop 40C. Signal 1 appears and remains at the Q outputs of the latter, and the open switching devices 33C and 34C are switched over to their closed position. Consequently, counter 11C starts counting the pulses of heart beats, while the counter 20C starts to count time intervals generated by the clock 15, and the divider 46C computes and displays the frequency of heart beats of the user for those physical actions whose spacings are equal to the width of the channel C of the unit 23.

For the sake of simplicity, further modes of operation of the heart beat monitor are explained hereinbelow with reference to the channel C, since the actions in all other channels are similar to the actions in the selected channel C.

During the monitoring time each of the counters 11 displays on its display device the total number of heart beats N, for example in the channel pertaining to the width $\tau_c$ N=$N_c$. Each counter 20 displays the total time T during which the number N of impulses is accumulated, for example for the channel width $\tau_c$ T=$T_c$. The divider 46 in each channel shows the frequency of heart beats. For example for the channel C $$v_c = \frac{N_c}{T_c}$$

In accordance with the width of channel $\tau$ in which the frequency of the heart beats is computed, it is possible to determine the functional dependence of the frequency of heart beats on the time interval $\tau$ between the succesice cycles of physical actions or loads $$v = f(\tau)$$

In particular, for the cycles of physical actions which are performed with the time intervals $\tau_c$, the divider 46C displays the magnitude $v_c$. This read out is analogous for other time intervals between the cycles of actions (exercises). Thus in the second mode for various time intervals between the cycles of actions, it is possible to determine:

Number of performed physical actions, separately for various time intervals between the cycles of actions N;

Total time duration of performance of the actions with different time intervals between the cycles T;

Frequency of heart beats during performance of the actions with different time intervals between the cycles $v$.

In the third mode of operation the monitor measures the frequency of heart beats in dependence on the number of performed actions. By means of the switch 7A the rate of counting of physical actions is set. At the beginning of the measurements signal 1 appears at the output of the first stage of the shift register 38. Through the switch 39A the signal 1 is supplied to the controlling inputs of the switching devices 33E and 34E and the latter are switched to the closed condition. The pulse counter 11E counts the number of physical actions $N_{1,r}$, and the counter 20E counts the time $T_{1,r}$ of performing these actions, while the divider 46E shows the frequency $v_{1,r}$ of the heart beats. When the counter 5 has counted r impulses and r cycles of physical actions, the signal 1 appears at the arm of switch 7A, and is applied through the closed switch 37 to the zeroing input of the counter 5. Simultaneously, this signal 1 is supplied through terminal 36.2 to the input of the shift register 38. As a result, the counter 5 starts again counting pulses, while the signal 1 passes from the first stage to the input of the second stage of the shift register 38 and through the switch 39B is supplied to the controlling inputs of the switching devices 33D and 34D which change to closed condition, while switching devices 33E and 34E change to open condition. In the channel E the counter 20E shows the time during which the physical actions have been performed from 1-st to r-th $T_{1,r}$ and the divider 46E shows the frequency of impulses $v_{1,r}$ during performance of first r cycles of actions $$v_{1,r} = \frac{N_{1,r}}{T_{1,r}}$$

After the termination of 2r impulses, for the second time the impulse is supplied to the data zeroing input of the counter 5 and to the input of the shift register 38. As a result of this, a new counting of impulses and cycles of physical actions starts in the counter 5, and the signal 1 passes from the output of the second stage to the input of the third stage of the shift register 38. The switching devices 33C and 34C change to conducting condition and this process continues in the aforedescribed manner. After performance of 2r physical actions, in the channel D the counter 20D shows the time $T_{r+1,2r}$ of performance of the actions from (r+1)-th to 2r-th, and the divider 46D shows the average frequency of impulses $v_{r+1, 2r}$ for the impulses from r+1 to 2r $$v_{r+1,2r} = \frac{N_{r+1,2r}}{T_{r+1,2r}}$$

wherein $N_{r+1,2r}$ is the number of heart beats during the time of performance of physical actions from (r+1)-th to 2r-th. Thus in each subsequent channel, the counter 20 shows the time duration of performance of subsequent cycles of actions T and average frequency of heart beats during their performance $v$.

In the third mode of operation the measurements can be performed for a selected total number of physical actions. For this purpose, instead of terminals 4.1 and 4.2, terminals 4.3 and 4.4 must be closed on the switch 4. In the fourth mode, in contrast to the third mode, the change of channels takes place not after respective cycles of actions, but after each time interval t. Magnitude of the time interval t is set by switch 7B. After elapsing of the time interval t from the beginning of time counting, signal 1 appears at the arm of the switch 7B, and this signal is supplied to the resetting input of the clock pulse generator 15, and counting of the time interval is restored. The signal 1 is also supplied through the terminal 36.1 to the input of the shift register 38, causing a shift of the signal 1 by one stage. In the fourth mode in each channel the frequency of impulses of pulse beats is counted, and in i-th channel the frequency of impulses related to the i-th time interval t from the beginning of performance of physical exercises.

The reading shown on the display panel will now be explained in detail with reference to FIG. 2.

In the first mode of setting the switches, as mentioned before, the device of the present invention operates in the same manner as that of the U.S. Pat. No. 4,489,731.

In the second mode of setting the switches each counter 11A-11E shows the number (from the beginning of the measurement) of the heart beats which have occurred during the same time periods when the intervals of time between the cycles of physical actions were equal in magnitude to the width of the channel of the histogram unit 23. The data of the counter are not affected by the order of alternating of different intervals between the cycles of physical actions. Each of the counters 20A-20E in the time channel in which it is incorporated shows a total elapsed time of counting of heart beats counted by the respective counters 11A-11E. Each divider 46A-46E shows on its display the frequency of heart beats during the performance of physical exercises (cycles) whose time intervals correspond to the width of a channel in which a divider is incorporated.

In the third mode of setting of switches each counter 11A-11E shows the number of heart beats during the time of performance of a series r cycles of physical exercises $$N_{kr+1,(k+1)r}$$

wherein k=0,1,2, ..., n, the number of even counts of r-physical actions. For the example shown in FIG. 1, k=0 for the channel E, k=1 for the channel D, k=2 for the channel C, k=3 for the channel B and k=4 for the channel A. When the order of connections of outputs of the shift register 38 is reversed, k=0 for the channel A, k=1 for the channel B, etc. Each counter 20A-20E shows the duration of the time of performance of a series r of physical exercises corresponding to $$T_{k\,r+1,\,(k+1)\,r}$$

Each divider 46A-46E in the same channel as the counter 11A-11E and 20A-20E shows an average frequency of heart beats in correspondence with the number of series each of r performed actions $$v_{kr+1,(k+1)r} = \frac{N_{kr+1,(k+1)r}}{T_{kr+1,(k+1)r}}$$

Therefore with k=0 the divider 46E still show the average frequency of heart beats during performance of first series of physical action from 1st to r-th, the divider 46D will show the average frequency of heart beats during performance of second series of physical actions from r+1 to 2r-th, the divider 46C will show the average frequency of pulse beats during performance of third series of physical exercises from (2r+1)-th to 3r-th, etc.

In the fourth mode os setting the switches each counter 11A-11E shows the number of heart beats during equal time intervals $t - N_{kt+1,(k+1)t}$, wherein k is the same as in the third mode. Each counter 20A-20E shows the duration of time of performance of actions from the beginning of measurements $T_{kt+1,(k+1)t}$. Each divider 46A-46E in the same channel as a counter 11A-11E and 20A-20E shows the average frequency of pulses in dependence on the duration of time of performance of physical actions $$v_{kt+1,(k+1)t} = \frac{N_{kt+1,(k+1)t}}{T_{kt+1,(k+1)t}}$$

The application of the above described monitor is not limited only to monitoring of data which characterized the flow of heart beats. It can also be used for analysis of other impulse flows. For this purpose the detector 1 of the heart beats must be replaced by another impulse detector or sensor of the required pick-up characteristic. For example, the detector 1 of heart beats can be replaced by a sensor of time periods of inhallation or exhallation. In this case the monitor will show the data which characterize the process of breathing, in the same way as it is carried out for the heart beats. If the impulse sensor of heart beats 1 is retained as shown in FIG. 1, but instead of the sensor 30 of cycles of physical exercises an impulse sensor of time periods of breating is used, it is possible to determine both the functional relationship between the breathing process of the heart beat of a patient, and also other characteristics of heart beats. When the two impulse sensors are interchanged, inverse functional relationship can also be obtained. The monitor can be used for determination of relationship between any processes represented by impulse flows. If the processes are represented by analog values, they must first be converted by A/D convertors and then they can be analysed in the described manner.

The invention is not limited to the deatils shown since various modifications and structural changes are possible without departing from the spirit of the invention.

I claim:

1. A pulse rate monitor for analyzing two concurrent pulse sequences, comprising
   a first detector for a first sequence of pulses;

an electronic histogram unit having an input and a plurality of output channels corresponding to predetermined pulse spacings;

a set of first counters and a set of second counters each having a data input and a plurality of data outputs and each being provided with display means, said first and second counters being assigned to respective output channels of said histogram unit;

a set of dividers connected between the outputs of said first and second counters to produce quotients of counts of the latter, each of said dividers being provided with display means;

a clock pulse generator;

a second detector for a second sequence of pulses;

switching means having a first switching position in which said first detector is connected to the input of said histogram unit, the inputs of said first counters are connected respectively to said output channels and said second counters being connected in series with said generator, and a second switching position in which said first detector is connected to each input of said first counters, said second detector is connected to the input of said histogram unit, and the inputs of said second counters are connected to an output of said clock pulse generator; and control means for controlling the connection between said first detector to said first counters, and the connection between said clock pulse generator and said second counters to activate in the second position of said switching means, those first and second counters which pertain to an active output channel of said histogram unit.

2. A pulse rate monitor as defined in claim 1, wherein said control means includes a set of normally open first switching devices provided in connections between said first detector and the inputs of respective first counters, a set of normally open second switching devices provided in a connection between an output of said clock pulse generator and the inputs of said second counters, each of said first and second switching devices having a control input, and coupling means connected between respective output channels of said histogram unit and said control inputs of said first and second switching devices.

3. A pulse rate monitor as defined in claim 2; further comprising a shift register having a data input and as many output stages as many output channels are in said histogram unit, means for connecting said data input of said clock pulse generator, and said output stages to respective control inputs of said first and second switching devices.

4. A pulse rate monitor as defined in claim 2, wherein said coupling means includes a set of flip-flops each having a Q output connected to control inputs of a pair of said switching devices, a resetting input connectable via a switch to an assigned output channel and a setting input connected via a delay element to said assigned output channel of the histogram unit.

5. A pulse rate monitor as defined in claim 1; further comprising a recounting device connected to said second detector and operating with recounting factor $k=1,2 \ldots n$ to pass each k-th pulse from said second sequence of pulses.

6. A pulse rate monitor as defined in claim 1; further comprising a panel provided with a plurality of windows for the display means of said first and second counters and of said dividers, said windows forming an array in which the display means pertaining to an output channel of said histogram unit are arranged at correlated locations.

7. A pulse rate monitor as defined in claim 1, wherein said first detector is a heart beat detector and said second detector detects physical actions performed by the user of the first detector.

8. A pulse rate monitor as defined in claim 7, wherein said first detector detects time periods of inhallation or exhallation.

* * * * *